(12) United States Patent
Laufer

(10) Patent No.: US 8,870,821 B2
(45) Date of Patent: Oct. 28, 2014

(54) DEVICE FOR TISSUE INJECTION

(76) Inventor: Michael D. Laufer, Menlo Park, CA (US)

( * ) Notice: Subject to any disclaimer, the term of this patent is extended or adjusted under 35 U.S.C. 154(b) by 176 days.

(21) Appl. No.: 11/549,454

(22) Filed: Oct. 13, 2006

(65) Prior Publication Data

US 2008/0091149 A1    Apr. 17, 2008

(51) Int. Cl.
*A61M 37/00*    (2006.01)

(52) U.S. Cl.
CPC .................................... *A61M 37/00* (2013.01)
USPC ......................................................... 604/131

(58) Field of Classification Search
USPC .......... 604/181, 187, 246–256, 110, 135, 131
See application file for complete search history.

(56) References Cited

U.S. PATENT DOCUMENTS

| | | | |
|---|---|---|---|
| 5,026,349 A | 6/1991 | Schmitz et al. | |
| 5,279,583 A | 1/1994 | Shober, Jr. et al. | |
| 5,391,151 A | 2/1995 | Wilmot | |
| 5,728,071 A | 3/1998 | Watson et al. | |
| 5,858,001 A * | 1/1999 | Tsals et al. | 604/135 |
| 5,993,412 A | 11/1999 | Deily et al. | |
| 6,500,150 B1 * | 12/2002 | Gross et al. | 604/131 |
| 6,524,284 B1 | 2/2003 | Marshall | |
| 6,830,560 B1 * | 12/2004 | Gross et al. | 604/143 |
| 6,981,961 B1 | 1/2006 | Navelier et al. | |
| 2005/0192530 A1 * | 9/2005 | Castellano | 604/70 |
| 2006/0106346 A1 * | 5/2006 | Sullivan et al. | 604/134 |
| 2006/0111671 A1 | 5/2006 | Klippenstein | |
| 2006/0142698 A1 * | 6/2006 | Ethelfeld | 604/157 |

* cited by examiner

*Primary Examiner* — Kami A Bosworth
*Assistant Examiner* — Imani Hayman
(74) *Attorney, Agent, or Firm* — Levine Bagade Han LLP

(57) ABSTRACT

A system for administering an injection is described. The invention consists of an adhesive patch with an integrated injector that controllably insets an injection needle and delivers the medication contained within the patch. Variations of the system may also subsequently and automatically retracts the needle, rendering the patch safely inert. In additional variations, a portion of the system may remain on the patient and function as a bandage.

21 Claims, 3 Drawing Sheets

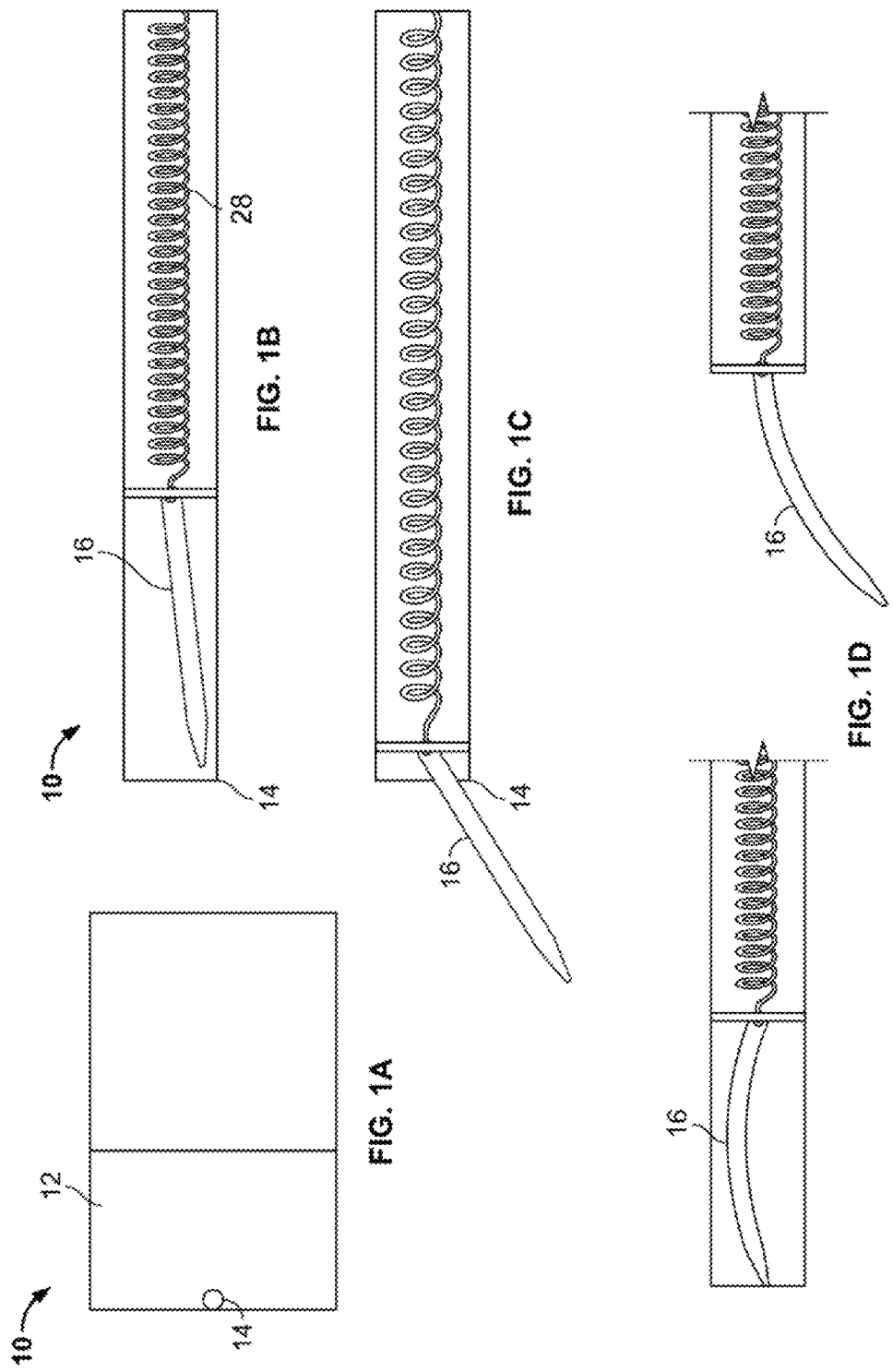

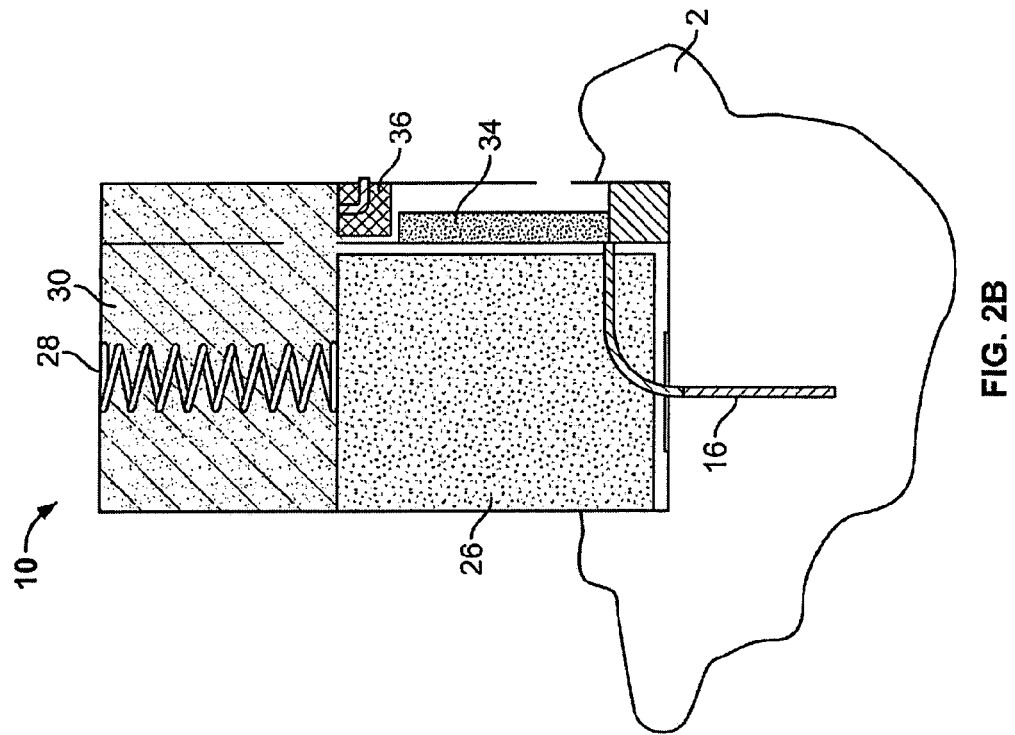
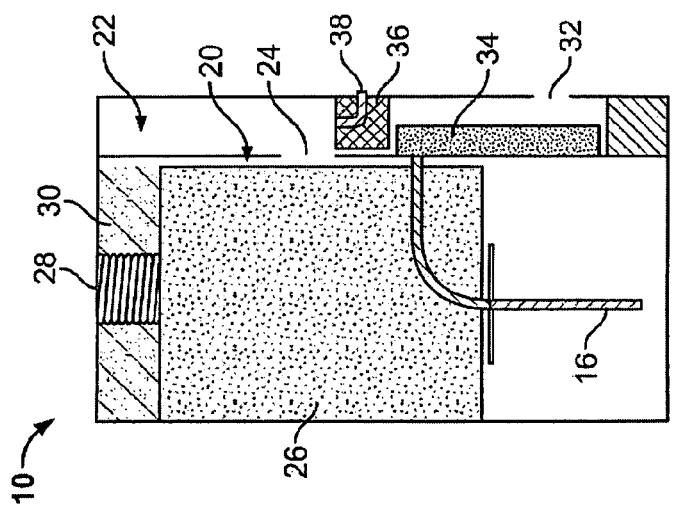

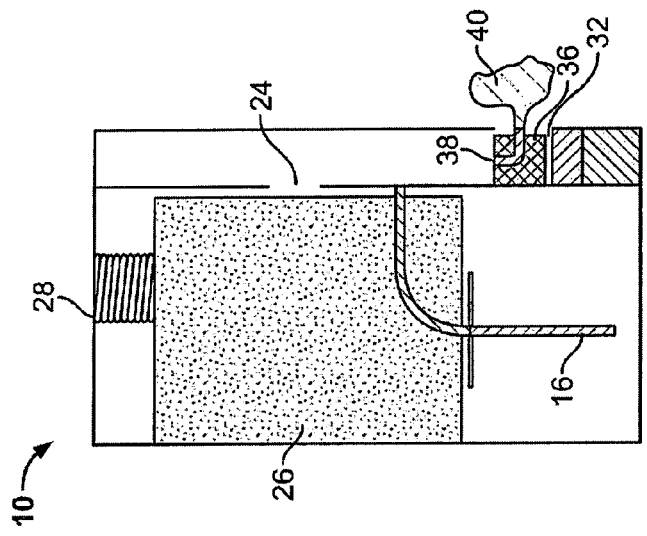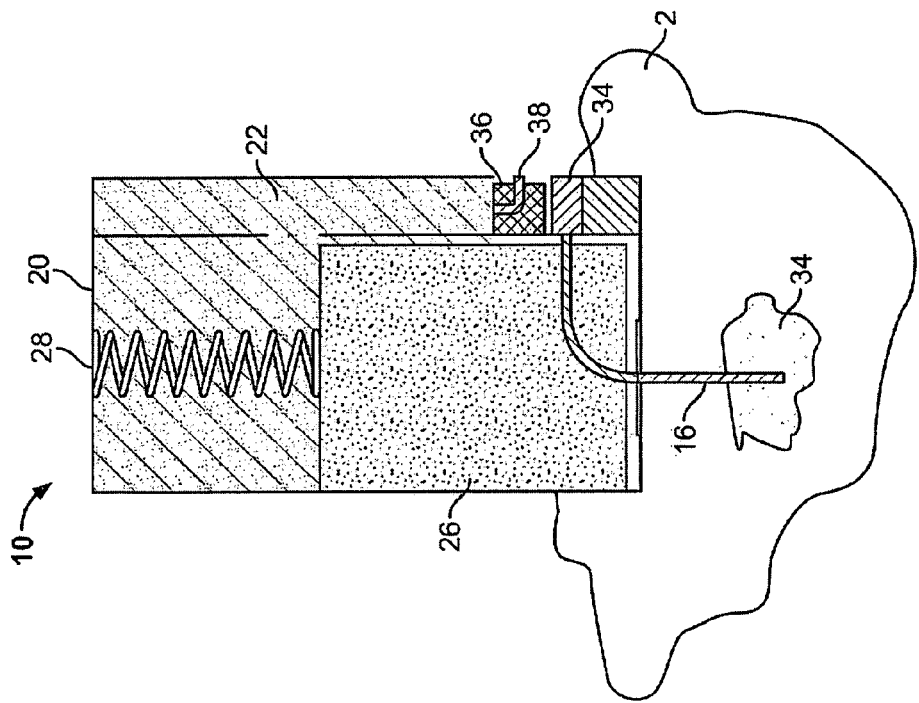

US 8,870,821 B2

DEVICE FOR TISSUE INJECTION

FIELD OF THE INVENTION

The present invention relates to an injection system for administering medical substances into tissue. Variations of the device and method described herein allow for an automated injector for administration of medications under the skin or into the muscle of patients. Further variations include injection systems designed to reside on an individual where injection of the substance can occur when needed and on-demand.

BACKGROUND

Several medications are frequently administered by injection into or under the skin with a syringe and needle system. Preferably, such injections require cleansing of the skin with alcohol or another antiseptic to prevent infection. The needle is then exposed and often visible to the patient. Next, the medical caregiver inserts the needle into the patient to a certain depth to inject the medication. The injection is then administered and the needle is withdrawn from the patient, leaving an exposed needle. Subsequently a bandage may be placed on the injection site.

Significant populations of individuals requiring such injections are frightened and/or react badly to the sight of needles. "Needle-less" pneumatic injectors were developed to obviate the need for needles. These systems are expensive and require regular maintenance. They have generally found application only in large-scale vaccination programs. If a patient moves during the administration of a pneumatic injection, failure of the injection and possible injury can result. Skin preparation prior to the injection and bandage application are still required as separate steps.

Standard needle/syringe injections are technique dependant. Both the rate of needle insertion as well as the rate of injection of the medication greatly affect the pain associated with the injection. Often, the needle is not inserted to the same depth resulting in bleeding, swelling, pain and potential ineffectiveness of the medication.

A syringe-loaded injection system is available currently for use primarily with emergency medications such as epinephrine. This "Epi-Pen" requires skin cleansing, uncapping, and forceful thrusting into the skin to actuate the spring firing mechanism. This injection system is rather large and awkward and is not easily carried, although it must be readily available in case the need for use arises. Users also complain that the spring-loaded mechanism sometimes fires accidentally and can result in an inadvertent injection with resultant injury.

Children receive multiple injections for vaccination against diseases and may require physical restraint in order to accomplish the injections. In view of the above, there remains room for improvement to injection systems, particularly medicinal injection systems.

BRIEF DESCRIPTION OF DRAWINGS

FIG. 1A shows a variation of an actuator/injection system.
FIG. 1B shows the needle residing within the system.
FIG. 1C show the needle exiting the system.
FIG. 1D shows a curved needle variation.
FIG. 2A shows a cross sectional view of a variation of the system prior to actuation.

FIG. 2B shows the system after the gas generation compound activates to increase the pressure within the first chamber.
FIG. 2C shows pressurization of a second chamber causing a drug delivery piston to compress the substance or medication.
FIG. 2D shows gas being vented through a venting port.

DETAILED DESCRIPTION

The present invention includes a simple self-contained injection system that can be applied to a patient. Although the system may be applied with traditional cleaning of the skin surface, variations include systems that, automatically prepare the skin with antiseptic. In a further variation of the system, the system allows injection of medication without further intervention at a standard rate of injection after a standard and optimal needle deployment, and can act as a bandage all in one application. Variations of the present system allow for safe and convenient carrying of the device prior to use. Variations of the system may include a self-retracting needle that leaves the used system safely inert.

FIG. 1A shows a variation of the invention. In this variation, the system 10 includes an actuator/injection system 10 where the system 10 includes an adhesive patch or section that is coated with an adhesive 12. Typically, the adhesive surface is initially covered with a removable backing. When applying the system 10 to an individual the backing is removed so that the system 10 adheres to the skin or clothing of the individual. As mentioned above, the adhesive section 12 may optionally be impregnated with any type of agent that may be required (e.g., an antiseptic agent, an anesthetic agent, clotting agent, etc., or a combination of agents if so desired). In the variation shown in FIG. 1, the system 10 contains an adhesive coating 12 on a portion of the system 10. In this case, the uncoated section of the system 10 may be unattached to the individual while the section with the needle opening 14 contains the adhesive. As discussed below, such a configuration may be desirable when repositioning the system 10 to prepare for an injection. Although other variations are possible, in such a variation the area of the system that delivers the needle is affixed to the injection area.

Next, the actuator/injection system 10 is activated to prepare for the injection. This activation may be initiated by manually repositioning part of the device (e.g., pulling the unaffixed portion perpendicular to the injection site). Alternatively, the system may be designed to reposition automatically (e.g., by pushing a button that electrically, chemically, or via a combination of means repositions the system to deliver the injection). Regardless, repositioning of the system may not be necessary.

Variations of the invention may be configured to deliver the injection upon repositioning of the system 10. However, the injection process may occur as a separate step as well. As shown in FIG. 1B, prior to injection, the needle 16 resides within the system 10. During actuation of the needle, but prior to the injection process, the needle 16 a needle/injection port 14 as shown in FIG. 1C. The needle/injection port may be a thin membrane that is penetrated by the needle upon actuation. In additional variations, the needle/injection port may be a valve-type member or simply an opening in the system.

As shown in FIG. 1C or 1D, needles 16 of the present system may be inclined, angled, or curved as well as straight. Such configurations may facilitate systems 10 that lay flat against the skin.

It is understood that in variations of the device, the needle port as well as the exit path of the needle may vary as required for the particular application. Furthermore, during the injection process can be triggered to automatically inject the medication. Such triggering mechanisms may be electrical, magnetic, manual, or fluid powered. In one variation, the injection process may be a gas generation process that is started when an activator is added to the gas generation compound. An example of such a compound is sodium bicarbonate with an activator consisting of, for example, acetic acid solution. For example, the two agents may be placed in separate compartments of the system 10 where actuation causes a separating member or wall to rupture to mix the agents.

FIG. 2A shows a cross sectional view of a variation of the system 10 prior to actuation. As shown, the system 10 includes a first chamber 20, a second chamber 22 and a port 24 that allows for eventual equalization of pressure between the two chambers. The needle 16 resides in the first chamber 20 and is coupled to a sealing piston 26 that temporarily blocks the port 24. To actuate the system 10 the gas generation compound 30 drives the sealing piston 26 and needle 16. Eventually, the needle 16 exits the system 10 via the needle port 14 as discussed below. The second chamber 22 contains the injection or therapeutic substance 34, an exhaust port 32 and a venting port 36. A spring 28 is affixed to the sealing piston 26 so that after the chamber decreases in pressure, the sealing piston 26 retracts causing the needle to withdraw. As the gas moves the sealing piston and needle assembly toward the skin, the spring stretches. Alternatively, the spring could be placed on the opposite side of the piston as a compression spring. The therapeutic substance may be held in a container or may be placed directly into the chamber 22.

FIG. 2B shows the system of FIG. 2B after the gas generation compound activates to increase the pressure within the first chamber 20. As shown, the increase in pressure causes the sealing piston 26 and needle 16 to advance (e.g., into the tissue 2). Once the proximal end of the sealing piston 26 moves past the chamber port 24, the second chamber 22 pressurizes.

As shown in FIG. 2C, pressurization of the second chamber 22 causes a drug delivery piston 36 to compress the substance or medication 34. As shown, the medication is in fluid communication with the needle 16. Accordingly, compression of the medication 34 results in injection of the substance 34 into tissue (as shown.) In another variation, the system may not require a piston 36 to compress the substance 34 (or a container holding the substance). Instead, the system will be configured so that pressure generated within the second chamber 22 compresses the substance 34 moving it through the needle 16.

As shown in FIG. 2D, the delivery piston 36 includes a venting port 38. Once the pressure drives the piston 38 a sufficient distance to inject the substance 34, the venting port 38 becomes exposed to the atmosphere via an exhaust port 32. Accordingly, gas 40 from the system 10 exhausts from the port 32 to cause a pressure decrease in the first and second chambers 20 and 22. As the pressure decreases, insertion force exerted against the sealing piston 26 decreases as well. Once this insertion force drops below the return force exerted by the spring 28 on the sealing piston 26, the return force or spring causes the sealing piston 26 to return. It should be noted that the back of the first chamber 20 may include a deformable one-way valve located between the first and second chambers. The deformable valve could permanently open after injection of the medicine to prevent residual pressure from impeding retraction of the sealing piston 26 and needle 16.

The rate of needle deployment can be controlled as desired. For example, the rate of deployment may be controlled by selecting substances having varying rates of gas creation. Alternatively, the rate of deployment may be altered by changing the force of the return spring or the frictional force acting on the needle piston. Likewise, the rate of medication delivery can be manipulated and controlled by adjusting the resistance of the chamber port between the first and second chambers 20 and 22, by the resistance to flow through the fluid channel into and through the needle, and/or by the friction and momentum of the drug delivery piston and the force needed for drug reservoir compression. The system may be designed to delay the injection to allow the anesthetic/analgesic time to work before needle deployment but after actuation.

The system 10 can be configured so the sound of the exhaust 40 is audible, such as a whistle. The audible signal provides the patient and/or staff completion of the injection.

In addition to the above discussion, the invention includes, but is not limited to the following:

A method of beginning an injection consisting of placing an adhesive patch with or without antiseptic and/or anesthetic components, onto an area of the skin, activating the injection system and delivering the medication through said injection system, after which the needle is retracted into the system to render it inert.

In the above method the event may comprise generating a signal in response the completion of the injection process.

The devices described herein generally automatically administer an injection into the skin where they are placed without the need for additional intervention on the part of the patient or medical practitioner. These devices generally include an adhesive patch. The patch may have an agent such as an antiseptic and/or anesthetic agent. The injection component includes a movable needle and a drug reservoir with a force-generating component such as a gas generator that is activated after or about the time of the desired injection.

In additional variations of the invention, the actuation mechanism may include a winding mechanism that stores energy via winding. The energy is then dissipated by the injection process. Alternatively, or in combination, an expandable polymer or hydrogel may be placed into the first and/or second chambers 20, 22. To activate the device, and expanding agent such as water or expanding foam is added to complete the injection process. In yet another variation, the pistons 26, 36 may be fabricated from the expandable polymer or hydrogel. In another variation, the device may use a hydrophilic material that allows the device to self-actuate after the backing is removed from the adhesive. This feature may allow for injection soon after the device is placed on an individual.

Naturally, the system may include a variation of the above configurations. Variations of the device may include systems that have various decorations on the outer surface to make the system more child-friendly and alleviate apprehension of getting an injection. In these devices and methods, the conditions may be those as described above, or other conditions as required by the specific treatment sought.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A system for delivering an injection into tissue, the system comprising:

a body having an exterior surface, the body containing a first chamber and a second chamber;

the first chamber comprising a needle affixed to a first piston, where the needle and first piston are slidably located in the first chamber where the needle is configured to be slidable upon movement by the piston;

the second chamber containing a therapeutic substance, where the therapeutic substance is in fluid communication with the needle;

a first port in fluid communication with the first chamber and second chamber, where a body of the first piston blocks the first port;

a pressure generating compound located within at least the first chamber, such that upon generating pressure, the pressure drives the first piston to cause movement of the needle so that the needle is advanced out of the body and into tissue and subsequently causes movement of the therapeutic substance through the needle; and an adhesive located on the exterior surface.

2. The system of claim 1, further comprising a second piston where upon generating pressure, the pressure drives the second piston against the therapeutic substance to deliver the substance through the needle.

3. The system of claim 2, where the body comprises an exhaust port, and where the second piston comprises a venting port in fluid communication with at least the second chamber, such that when the venting port is moved in fluid communication with the exhaust port, the venting port and exhaust port exhausts the pressure from within the body.

4. The system of claim 3, further comprising an audible noise generator configured to generate an audible noise as gas exhausts from the exhaust port.

5. The system of claim 1, further comprising a spring mechanism coupled to the first piston such that upon the generation of pressure, the spring resists movement of the first piston and upon decrease in pressure, the spring retracts the first piston and needle.

6. The system of claim 5, where the spring comprises a compression spring.

7. The system of claim 1, further comprising an agent located on an exterior of the injection system.

8. The system of claim 7, where the agent is selected from a group consisting of an antiseptic agent, an anesthetic agent, a clotting agent, and a combination of agents.

9. The system of claim 1, further comprising a seal and where the needle is driven through the seal when exiting the body.

10. The system of claim 9, where the needle is curved.

11. The system of claim 1, where the pressure generating compound comprises sodium bicarbonate.

12. The system of claim 11, further comprising an activator compound to activate the pressure generating compound.

13. The system of claim 12, where the activator compound comprises an acetic acid solution.

14. The system of claim 1, where the pressure generating compound comprises a gas generating compound located within at least the first chamber, such that upon generating pressure, the pressure drives the first piston and the needle so that the needle is advanced out of the body and into tissue and subsequently causes movement of the therapeutic substance through the needle.

15. The system of claim 1, where the where the pressure generating compound increase the pressure within the first chamber.

16. A system for delivering an injection into tissue, the system comprising;

a body having an exterior surface, the body containing a first and a second chamber;

the first chamber comprising a needle affixed to a first piston, where the needle and first piston are slidably located in the first chamber where the needle is configured to be slidable upon movement by the piston;

the second chamber containing a therapeutic substance, where the therapeutic substance is in fluid communication with the needle;

a first port in fluid communication with the first chamber and second chamber, where a body of the first piston blocks the first port; and a pressure generating compound located within at least the first chamber, such that upon generating pressure, the pressure drives the first piston to cause movement of the needle so that the needle is advanced out of the body and into tissue and subsequently causes movement of the therapeutic substance through the needle.

17. The system of claim 15, further comprising a second piston where upon generating pressure, the pressure drives the second piston against the therapeutic substance to deliver the substance through the needle.

18. The system of claim 16, where the body comprises an exhaust port, and where the second piston comprises a venting on in fluid communication with at least the second chamber, such that when the venting port is moved in fluid communication with the exhaust port, the venting port and exhaust port exhausts the pressure from within the body.

19. The system of claim 15, further comprising a spring mechanism coupled to the first piston such that upon the generation of pressure, the spring resists movement of the first piston and upon decrease in pressure, the spring retracts, the first piston and needle.

20. The system of claim 15, further comprising an agent located on an exterior of the injection system.

21. The system of claim 15, further comprising a seal and where the needle is driven through the seal when exiting the body.

* * * * *